US006063765A

United States Patent [19]

Bennich et al.

[11] Patent Number: 6,063,765

[45] Date of Patent: May 16, 2000

[54] ANTIBACTERIAL PROTEIN

[76] Inventors: Hans Bennich, 3622 W. Eagle's View Pl., Tucson, Ariz. 85745; Andreas Axén, Stenberga, S-740 21 Järlåsa, Sweden; Anette Carlsson, Dirigentvägen 185, S-756 54 Uppsala, Sweden; Åke Engström, Nyodlarvägen 27, S-740 22 Bälinge, Sweden

[21] Appl. No.: 09/014,574

[22] Filed: Jan. 28, 1998

[51] Int. Cl.[7] ............................ A61K 38/00; C07K 1/00; C07K 5/00; A10N 25/34

[52] U.S. Cl. ............................ 514/12; 530/300; 530/350; 424/404

[58] Field of Search .............................. 514/12; 530/300, 530/350; 424/404

[56] References Cited

FOREIGN PATENT DOCUMENTS 0856519 8/1998 European Pat. Off. ...... C07K 14/435

OTHER PUBLICATIONS

Spies, Karlinsey and Spence, "Antibacterial Hemolymph Proteins Of Manduca Sexta", Comp. Biochem. Physiol, vol. 83B, No. 1, pp. 125–133, 1986 Great Britain.

Axén et al., *Eur. J. Biochem*, vol. 247, pp. 614–619, 1997.

*Primary Examiner*—Avis M. Davenport

*Attorney, Agent, or Firm*—Young & Thompson

[57] ABSTRACT

The present invention relates to a novel antibacterial protein, called gloverin. Preferably, gloverin is isolated from Hyalophora moths. Alternatively, gloverin is produced by genetic engineering or by chemical synthesis.

Also, the invention relates to pharmaceutical compositions comprising gloverin or pharmaceutically active fragments thereof and use of gloverin or fragments thereof as a medicament against bacterial infection. Furthermore, the invention relates to a method of treating bacterial infection comprising administration of gloverin or pharmaceutically active fragments thereof.

19 Claims, 7 Drawing Sheets

Figure 2:
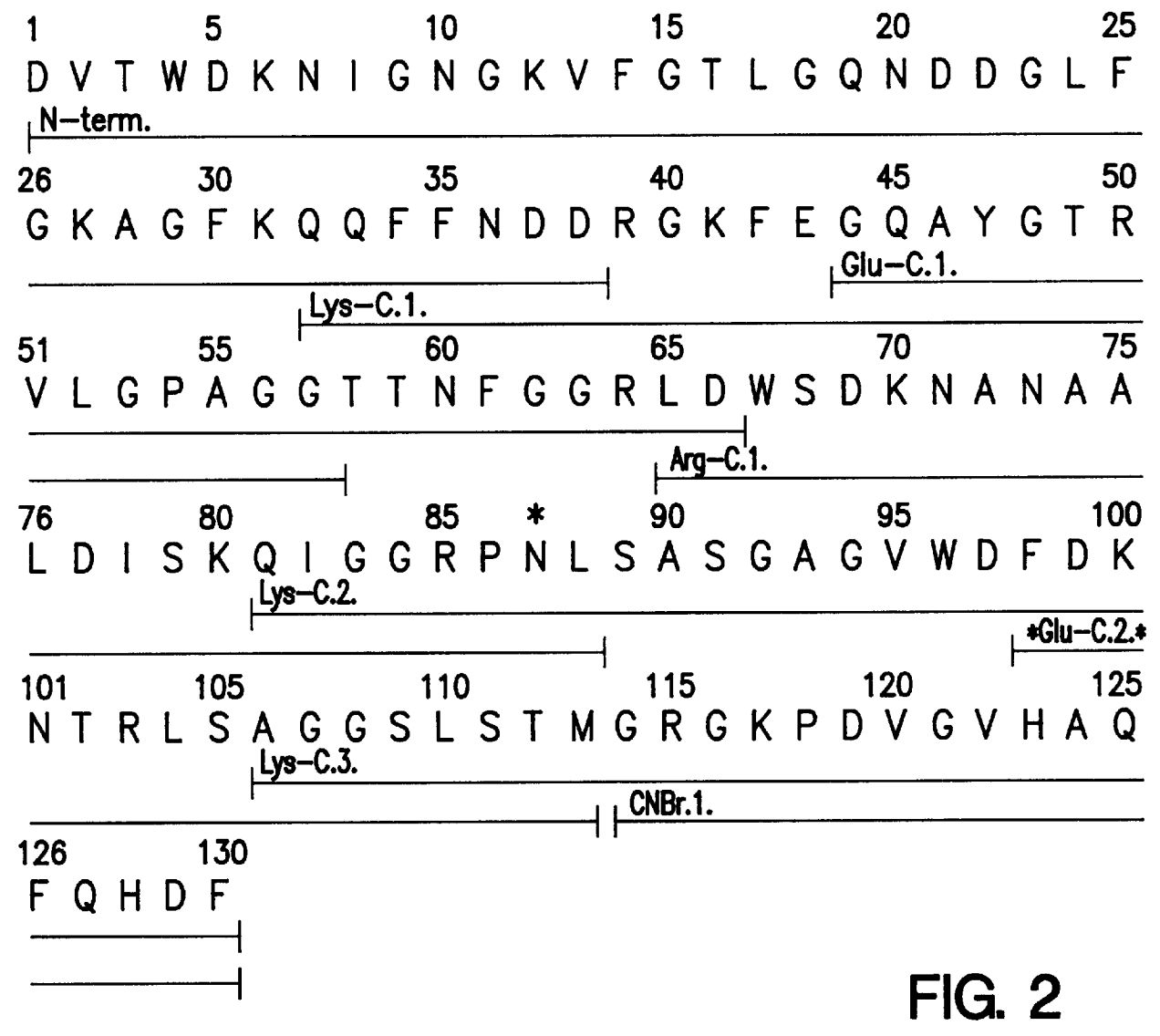

```
1       5         10        15        20        25
D V T W D K N I G N G K V F G T L G Q N D D G L F
N-term.

26      30        35        40        45        50
G K A G F K Q Q F F N D D R G K F E G Q A Y G T R
                                      Glu-C.1.
              Lys-C.1.

51      55        60        65        70        75
V L G P A G G T T N F G G R L D W S D K N A N A A
                              Arg-C.1.

76      80        85   *    90        95        100
L D I S K Q I G G R P N L S A S G A G V W D F D K
          Lys-C.2.
                                            *Glu-C.2.*

101     105       110       115       120       125
N T R L S A G G S L S T M G R G K P D V G V H A Q
          Lys-C.3.
                            CNBr.1.

ANTIBACTERIAL PROTEIN

The present invention relates to a novel antibacterial protein, designated gloverin, representing a new class of antibacterial insect proteins which can be isolated from Lepidoptera, more specifically the pupa of Hyalophora giant silk moths.

Furthermore, the invention relates to pharmaceutical compositions comprising gloverin as a medicament and use thereof in a method against bacterial infection.

BACKGROUND OF THE INVENTION

Infection of pupae of lepidopterans with live non-pathogenic bacteria induces the synthesis of a variety of antibacterial polypeptides secreted into the hemolymph. Previous studies have identified three main classes of antibacterial proteins namely lysozyme, cecropins and attacins [1]. Lysozyme [2,3] attacks the cell wall of gram-positive bacteria. The small (4–5 kDa), cationic cecropins [3,4] display a strong bactericidal effect against a variety of gram-positive and gram-negative bacteria. The attacins [5,6,7] (20 kDa) exist in two forms; one basic (pl=9) and one neutral pl=7) and the antibacterial effect is directed only against gram-negative bacteria.

Several forms of these antibacterial proteins have been found in various insect species. Peptides related to cecropins can be found not only in insects but also in vertebrates [8]. The same is true for the ubiquitous lysozymes. A protein related to the attacins, sarcotoxin IIA, has been found in the dipteran Sarcophaga [9].

Another class of antibacterial proteins from insects is the insect defensins [10]. They are characterised by an amino acid sequence of 38 to 43 amino acids containing six cysteines, forming three disulphide bridges. Different variants of insect defensins have been found in several insect species. Other related insect proteins are the diptericins with a molecular mass of 8.6 kDa that are effective against gram-negative bacteria [11] and the hemolins that belong to the immunoglobulin superfamily and are suggested to play a role in the regulation of cell adhesion during the cellular response to bacterial infections [12,13].

In addition to the antibacterial proteins from insects, there is also a number of antibacterial proteins isolated from mammalians e.g. the bactericidal/permeability increasing protein (BPI) [14,15] and the defensins [16]. The mammalian defensins differ structurally from insect defensins, although they have similar size and charge.

SUMMARY OF THE INVENTION

The present invention provides a novel antibacterial protein, called gloverin. Gloverin is a basic (with a pl of about 9) protein with a molecular weight of about 14 kD containing a large number of glycine residues but no cystein. Gloverin displays no strong sequence similarity to other known proteins. Gloverin inhibits the growth of gram-negative bacteria, such as *Escherichia coli*. The minimal concentration required for inhibition of bacterial growth is 1–3 μM, which is less than 5% of the concentration of gloverin in the hemolymph of infected pupae. The synthesis of vital outer membrane proteins and, consequently, the permeability of the outer membrane are affected, indicating that the activity of gloverin is directed to the outer membrane of gram-negative bacteria.

Preferably, the novel antibacterial protein, gloverin, according to the invention is isolated from Hyalophora moths. Alternatively, gloverin is produced by genetic engineering or by chemical synthesis.

Also, the invention relates to pharmaceutical compositions comprising gloverin or pharmaceutically active fragments thereof and use of gloverin or fragments thereof as a medicament against bacterial infection. Furthermore, the invention relates to a method of treating bacterial infection comprising administration of gloverin or fragments thereof.

DETAILED DESCRIPTION OF THE INVENTION

Materials and Methods

Figure 1:
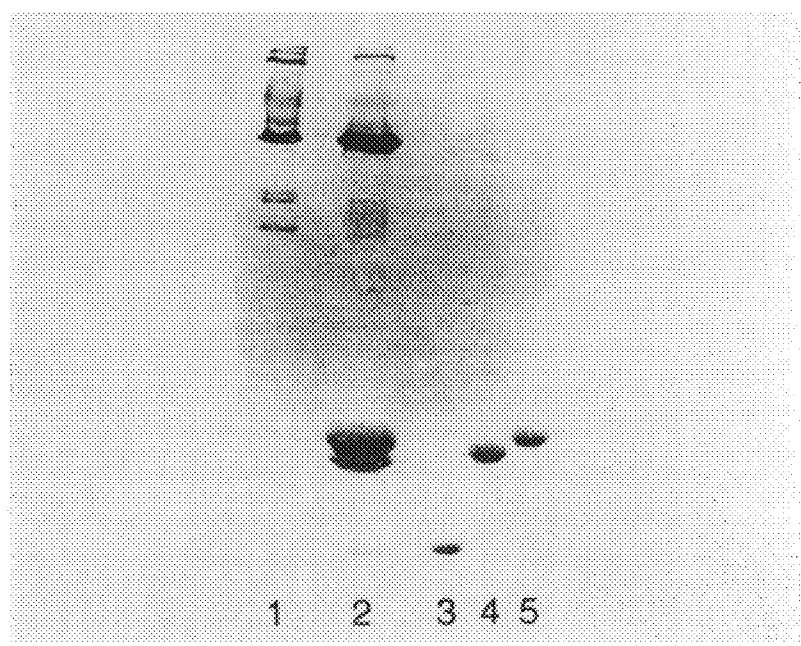

Isolation of protein. Diapausing pupae of *Hyalophora gloveri* were injected with 105 live *Enterobacter cloacae* β12. After 7 days the hemolymph was collected as previously described [3]. Gloverin was purified from freshly collected or frozen hemolymph by the following procedure: 50 ml hemolymph was diluted five times with ice-cold distilled water and centrifuged for 10 min at 17000×g, 4° C. Saturated ammonium sulphate (SAS) solution was added to the supernatant to give 25% SAS final concentration. After 30 min at room temperature the precipitate was collected by centrifugation for 10 min at 17000×g, 4° C. The precipitate was dissolved in 10 ml distilled water and desalted on a Sephadex G-25, PD-10 column (Pharmacia, Sweden) equilibrated with the starting buffer used in the subsequent ion-exchange chromatography step. This was performed on a DEAE-Sepharose CL-6B column (3×6 cm)(Pharmacia, Sweden) equilibrated with 20 mM diaminopropane, adjusted to pH 10.1 with hydrochloric acid, at room temperature. Proteins were eluted using a gradient of 1 M sodium chloride in starting buffer. A subsequent gel filtration step was performed on a Superdex-75 column (1×30 cm) (Pharmacia, Sweden) equilibrated with 0.1 M ammoniumbicarbonate.

Approximately 1.5 mg of purified gloverin were recovered from 50 ml of hemolymph collected from 50 pupae. The purity of the isolated protein was ascertained by sodium dodecyl sulphate-polyacrylamide gel electrophoresis (SDS-PAGE) and mass spectrometry as described below.

Electrophoresis. SDS-PAGE was performed in 12.5% (w/v) slab gels by the method of Laemmli [17] but with a 4.5% stacking gel, containing 9% glycerol. Isoelectric focusing was performed using a Phast system (Pharmacia, Sweden) following the manufacturers standard protocols.

Automated amino acid sequence analysis [18] was performed using an ABI 477A (Applied Biosystems) protein sequencer with an on-line ABI 120A PTH analyser following standard protocols.

Gloverin was cleaved using cyanogen bromide, Glu-C, Lys-C or Arg-C endoproteinase (Boehringer Mannheim). Following cleavage with cyanogen bromide or Glu-C endoproteinase the digest was separated on a Superdex-75 gel filtration column in 0.1 M ammoniumbicarbonate. When cleaved with Lys-C or Arg-C endoproteinase the digest was separated by RP-HPLC on a Brownlee C-18, 5 m column, 2.1×30 mm, eluted with a gradient of 0–70% acetonitrile in water containing 0.1% trifluoroacetic acid during 60 min with a flow rate of 0.3 ml/min.

Chromatography was carried out using an FPLC system (Pharmacia, Sweden). The effluent was monitored at 214 nm. All fractions collected were analysed by mass spectrometry.

Sequence comparison. The databases Swiss protein (release 27.0), and PIR protein (release 35.0) were searched by the program FASTA [19] using the Genetic computer group software [20].

Amino acid analysis. Amino acid analyses were performed by the ion exchange ninhydrin method.

Mass spectrometry. Plasma desorption mass spectra for cleavage products during sequence work were obtained using a BIOION 20 mass spectrometer (Applied Biosystems).

Circular dichroism. Circular dichroism (CD) measurements were performed on a Jasco 41A spectropolariometer. d-10 Camphor-sulphonic acid was used for calibration with D e taken as +2.37 at 290 nm. All spectra were recorded at 25° C. using a 0.1 cm cell. Protein concentrations used were 0.1 mg/ml for estimating the optimum concentration of hexafluoro-iso-propanol and 0.3 mg/ml for recording the complete spectra, respectively.

Protein concentrations were determined spectrophotometrically at 280 nm using the absorptive value of 18 350 M-1 cm−1. The mean residue ellipticity expressed in deg.cm/dmol was calculated at every nm and is given as the average of two analyses. The mean residue weight used was 106.4 g/mol.

NMR-analyses. 1D 1H-NMR analyses were performed on a Varian 400 MHz FT NMR spectrometer.

Ultracentrifugation. Equilibrium and sedimentation experiments were performed using an Optima XL-A (Beckman Inc.) analytical ultracentrifuge.

Bacterial strains. D21f2 [21] is a rfa mutant of the *E. coli* K-12 strain D21 [22], with a deep rough, heptose-less lipopolysaccharide (LPS) (=chemotype Re). The gram-positive strain used was *Bacillus megaterium* Bm 11 [23]. The term "deep rough" used herein means that the LPS chain is shortened.

Antibacterial assay. The antibacterial activity of purified gloverin was assayed by recording the growth of liquid cultures in microtiter plates (NUNC,Denmark), 200 $\mu$l/well. Gloverin was added to LB medium at 5–10 $\mu$M final concentration and this mixture was inoculated with $5\times10^6$ cells in mid-log phase. The cultures were incubated at 37° C. on a rotary shaker and growth was recorded every 20 min by monitoring the absorbance at 560 nm with a Titertek Multiskan spectrophotometer.

In some experiments samples were withdrawn from the growing cultures at different times and spread on LB agar plates to determine the correlation between number of viable cells and absorbance.

Radioactive labelling of bacterial proteins. Cells were grown as described above for the antibacterial assay except that LB was substituted with M9 minimal medium supplemented with 0.4% (w/v) glucose and amino acids, except methionine. L-[35S] methionine (>37 TBq/mmol; Amersham, UK) was added to the cultures after 2 h, to a final concentration of 25 $\mu$Ci/ml. Labelling was continued for 10 min and then stopped by the addition of trichloroacetic acid to a final concentration of 10% (w/v). The labelled and precipitated cells were analysed on SDS-PAGE and the dried gels were overlaid with Kodak X-omat AR-film and exposed for two days at room temperature.

The invention will now be described below with reference to the accompanying drawings, in which:

FIG. 1 represents SDS PAGE analysis of SDS-precipitated hemolymph and purified proteins. Lanes: (1) Non-immune hemolymph (2) immune hemoplymph at day 7 (3) purified gloverin (4) purified basic attacin (5) purified neutral attacin FIG. 2 The amino acid sequence of gloverin (SEQ ID NO:1). The peptides used for sequencing are underlined to show overlaps. The peptide obtained by cleavage with cyanogenbromide is designated "CNBr.1." The peptides obtained by digestion with endoproteinase Glu-C, Arg-C and Lys-C are designated "Glu-C.1–2.", "Arg-C.1. and "Lys-C.1–3.", respectively. A potential glycosylation site is indicated by *.

Figure 3:
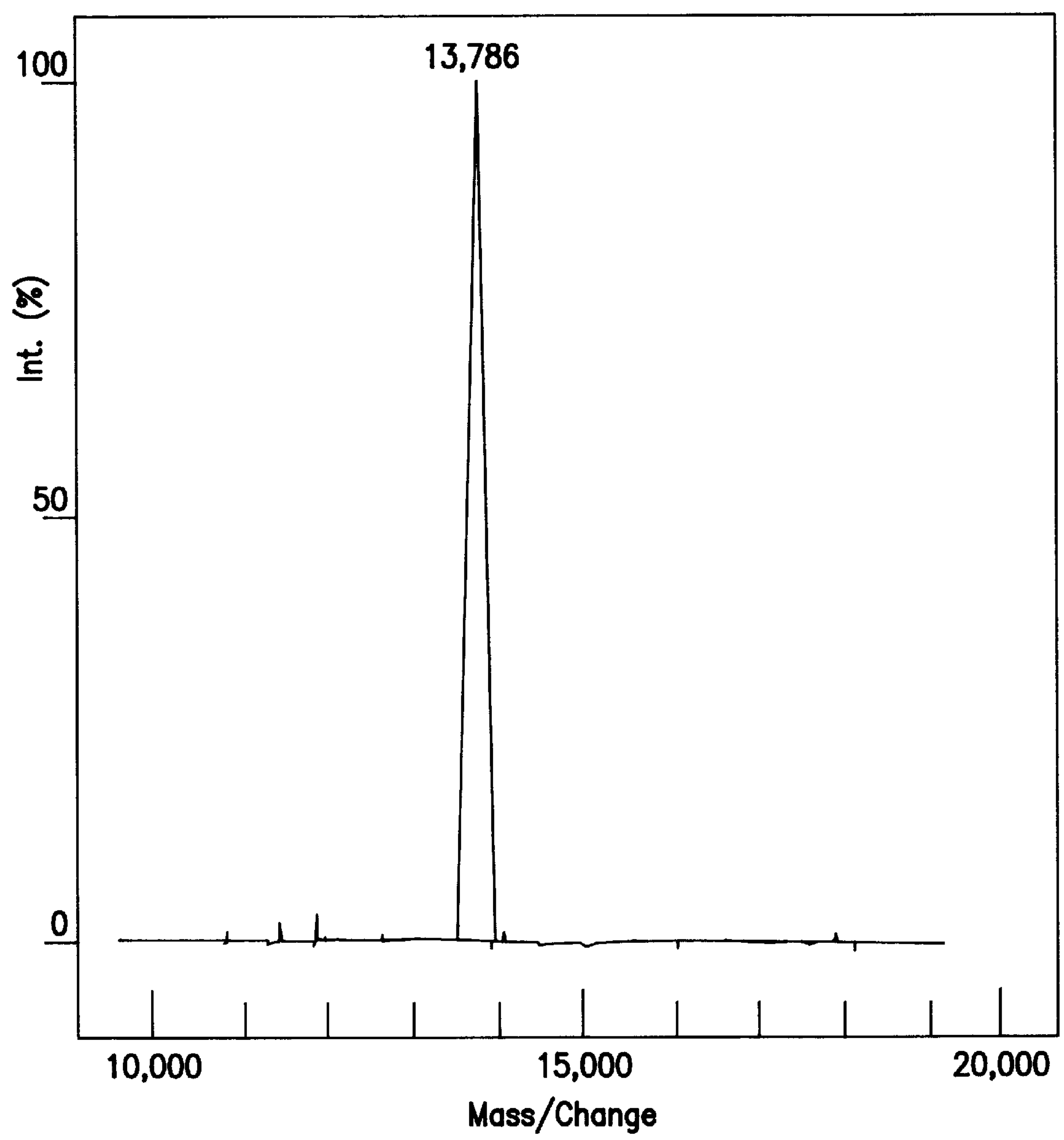

FIG. 3 Laser desorption mass spectrum for gloverin.

Figure 4:
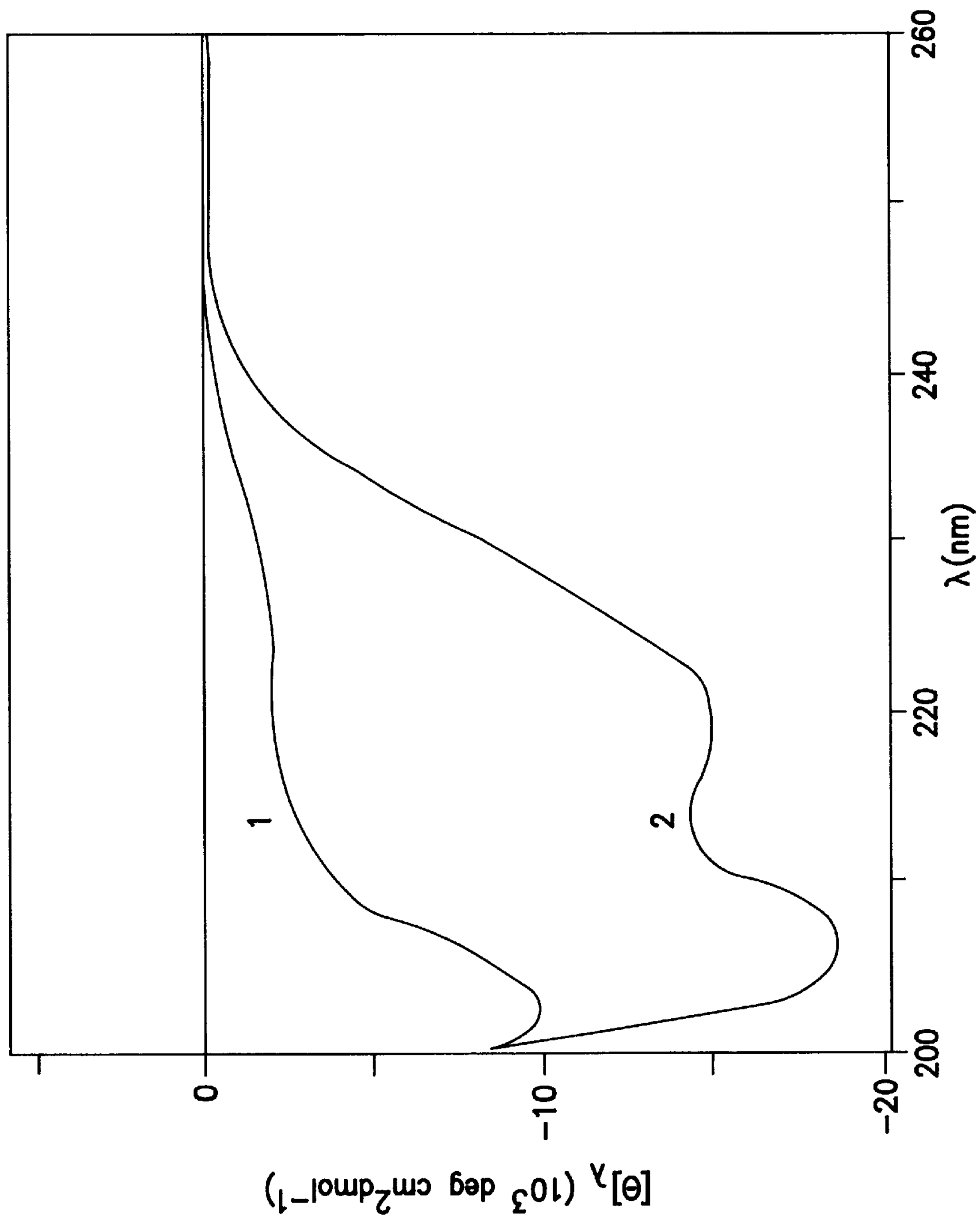

FIG. 4 Circular dichroism spectrum for gloverin. Gloverin dissolved in 10 mM phosphate pH 6.4 (1) and with the addition of 20% (v/v) hexafluoro-iso-propanol (2).

Figure 5:
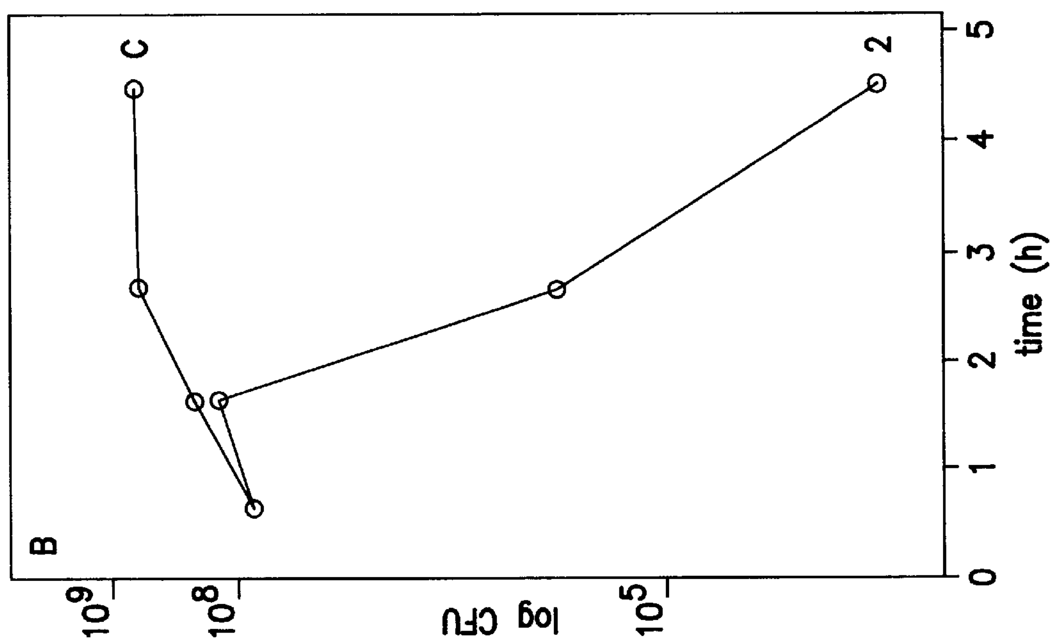
Figure 5:
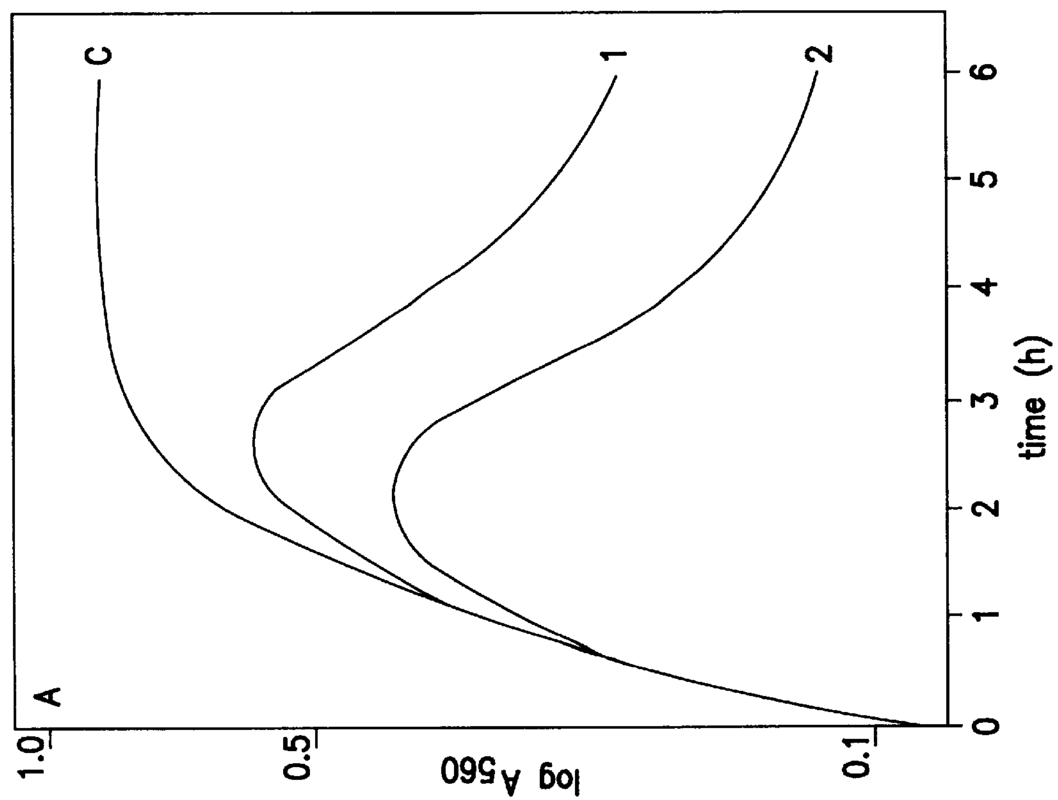

FIG. 5 Effect of gloverin on the growth of D21f2. Gloverin was added at time zero at a concentration of 5 mM (1) or 10 mM (2). The control (C) represents growth in the absence of gloverin. Panel A shows the optical density of the growing cultures. Panel B shows the number of viable cells in samples withdrawn from the cultures at times indicated.

Figure 6:
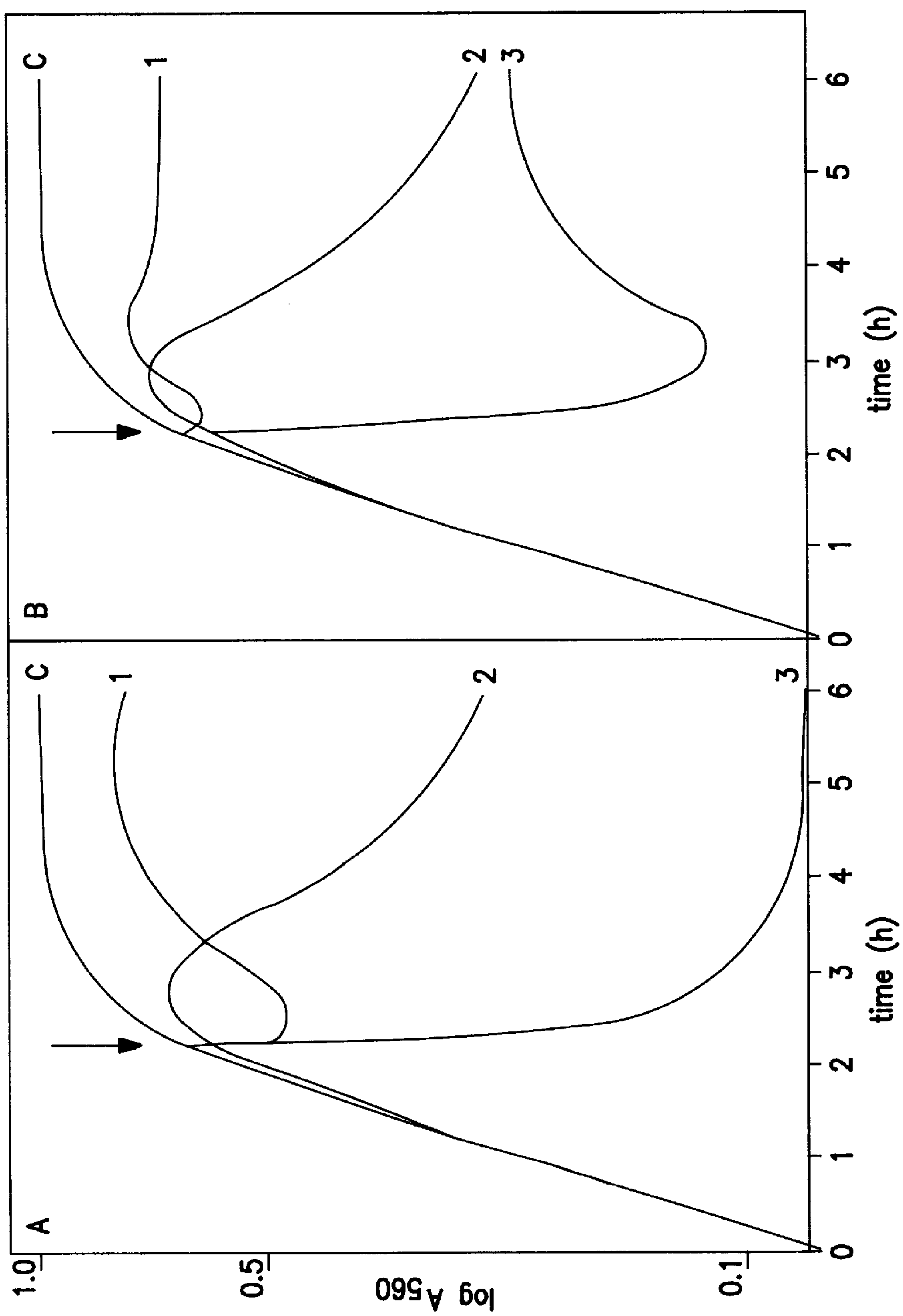

FIG. 6 Effect of Triton X-100 and lysozyme on D21f2 treated with gloverin. Triton X-100 (final concentration; 1% (w/v) (panel A); or chicken lysozyme (final concentration; 200 mg/ml) (panel B); was added at time indicated by arrow to cultures grown in the absence (1) or presence (3) of gloverin (5 $\mu$M). Curves (2) represent growth in the presence of gloverin (5 $\mu$M) only, and curves (C) are controls without any additions.

Figure 7:
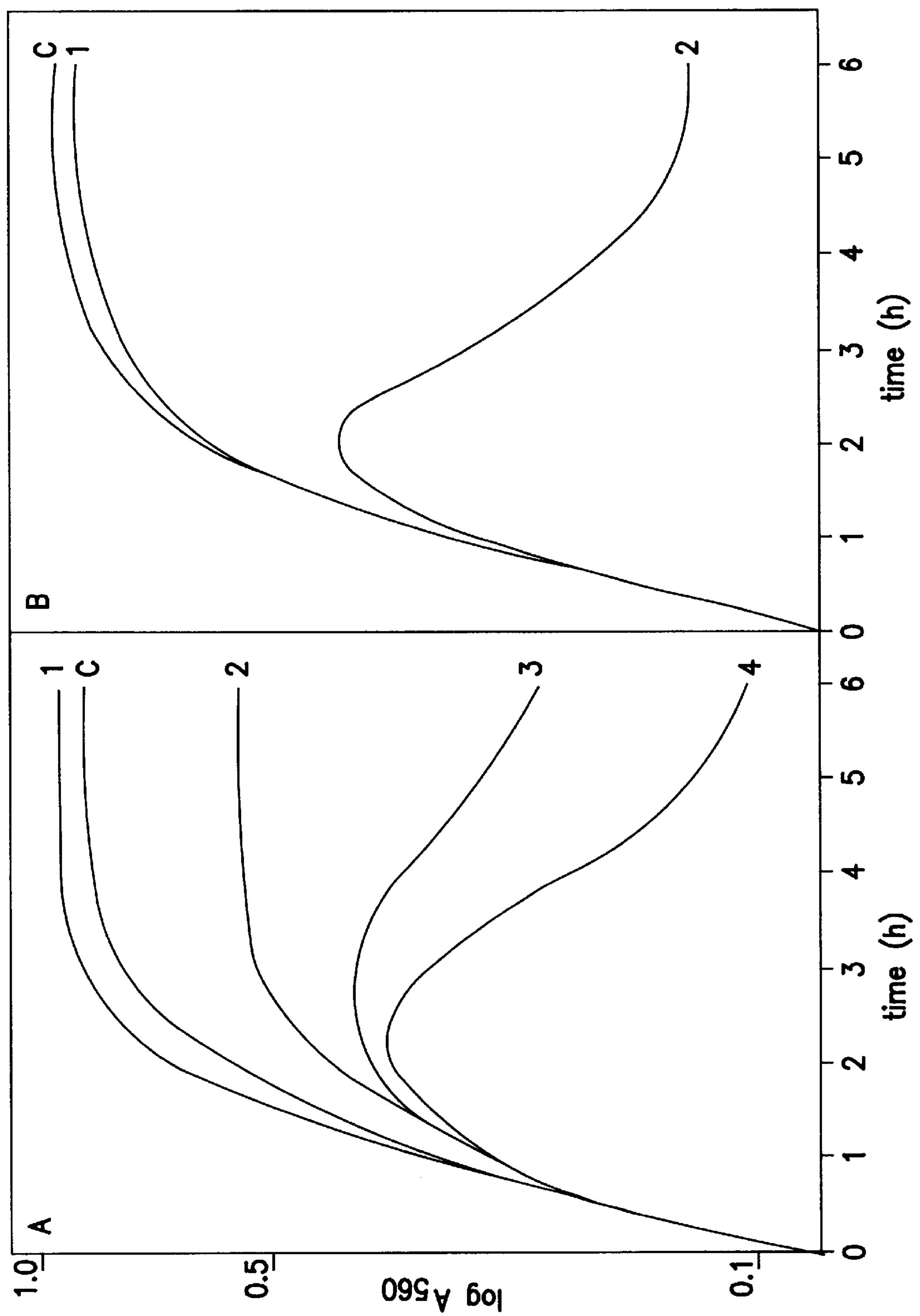

FIG. 7 Effect of lipopolysaccharide (LPS) and magnesium on the growth-inhibiting activity of gloverin on D21f2.

In panel A curve (1) represents growth with the addition of 50 $\mu$M of LPS. Curve (2) and (3) represent growth with the addition of 10 $\mu$M of gloverin and 50 $\mu$M or 30 $\mu$M of LPS, respectively. Curve (4) represents growth with the addition of 10 uM of gloverin solely and curve (C) represents the growth of D21f2 without any additives. In panel B curve (1) represents growth of D21f2 in the presence of 10 $\mu$M of gloverin and 40 mM $MgCL_2$. Curve (2) shows growth in 10 $\mu$M gloverin only and (C) represents the growth of D21f2 without any additives.

The addition of 40 mM $MgCL_2$ to the control culture has no effect (not shown).

Figure 8:
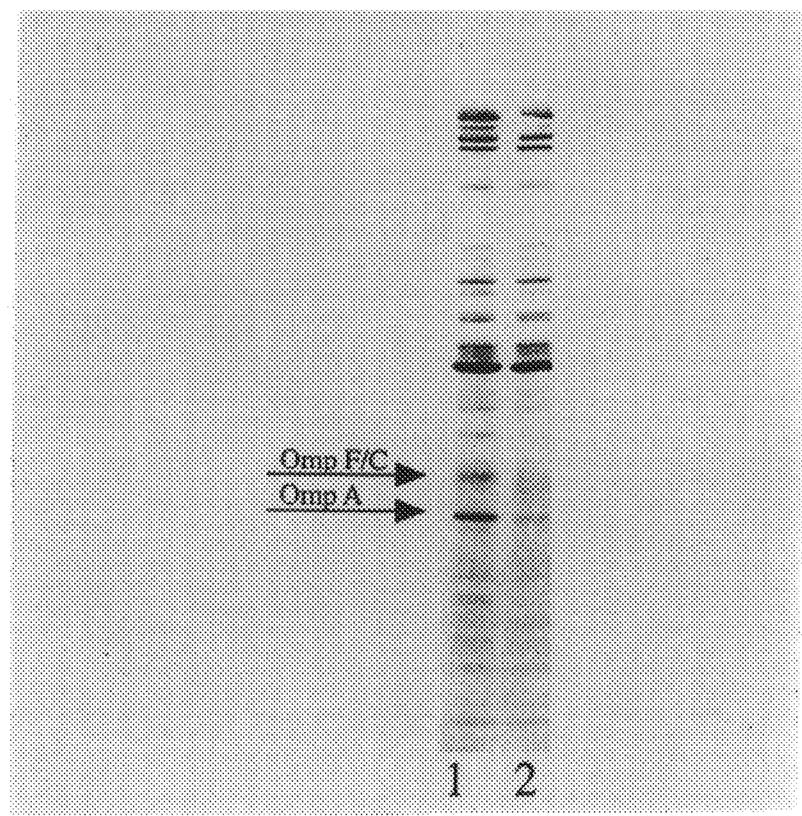

FIG. 8 Autoradiogram of SDS-PAGE showing the effect of gloverin on synthesis of the outer membrane proteins Omp F/C and Omp A.in 35S-methionine labelled D21f2 cells.

Lanes: (1) Control, untreated bacteria; (2) Bacteria incubated with gloverin (10 $\mu$M) for 2 h

RESULTS

Isolation of protein. Ion-exchange chromatography of ammonium sulphate precipitated immune hemolymph resulted in two large peaks as determined at 280 nm. Analysis by SDS-PAGE showed that the first eluted of these consisted of gloverin and the basic form of attacin, while the second peak contained the neutral form of attacin and some additional proteins (data not shown). In order to further separate gloverin from attacin the gloverin containing peak from the ion-exchanger was applied on a Superdex 75 column which yielded gloverin free of attacin.

The SDS-PAGE analysis (FIG. 1) of purified proteins and the hemolymph from immunised and non-immunised pupae demonstrates that gloverin is induced by infection. Isoelectric focusing showed that the purified gloverin has an isoelectric point of 8.5 (data not shown).

Sequence analysis. The amino acid sequence of the above described gloverin is shown in FIG. 2, which also includes the sequence of the different cleavage fragments used. One digestion with Glu-C endoprotease was by accident performed without sufficient buffering causing the enzyme to cleave after both glutamic acid and aspartic acid. This produced the peptide from amino acid 98 to 113 and gave an overlapping sequence in the region of amino acid number 100. Comparison of the sequence of gloverin with other sequences in current data banks revealed no proteins with strong sequence similarities.

With knowledge of the amino acid sequence it is possible to produce gloverin by chemical synthesis. The invention relates to gloverin and gloverin-like sequences. The main criterion is that the specific gloverin-activity is retained in the protein/fragment.

It is realized by the skilled man in the art that the DNA sequence encoding gloverin can be obtained from the above information. Thus, the invention also encompasses DNA sequences encoding gioverin and gloverin-like proteins. Furthermore, the invention relates to such proteins produced by conventional genetic engineering.

Amino acid analysis. The result of the amino acid analysis of gloverin is presented in Table 1 and is compared with the composition deduced from the sequence. Included is also the amino acid composition for the corresponding protein isolated from *Hyalophora cecropia*.

TABLE 1

Amino acid composition for gloverin

| Amino acid | Amino acid composition for glovering from *Hyalophora gloveri* according to sequense | Amino acid composition for glovering from *Hyalophora gloveri* according to a.a-analysis | Amino acid composition for glovering from *Hyalophora cecropia* according to a.a-analysis |
|---|---|---|---|
| Ala | 10 | 9,8 | 10,3 |
| Arg | 6 | 5,8 | 5,1 |
| Asn | 9 | | |
| Asp | 13 | 20,5 | 20,1 |
| Cys | 0 | 0 | 0,8 |
| Gln | 7 | | |
| Glu | 1 | 7,3 | 7,7 |
| Gly | 24 | 22,5 | 21,7 |
| His | 2 | 2,1 | 2,0 |
| Ile | 3 | 3,2 | 3,5 |
| Leu | 8 | 8,0 | 7,8 |
| Lys | 9 | 7,9 | 8,7 |
| Met | 1 | 1,1 | 1,2 |
| Phe | 10 | 9,7 | 9,4 |
| Pro | 3 | 3,3 | 3,8 |
| Ser | 7 | 7,2 | 7,4 |
| Thr | 7 | 6,8 | 7,3 |
| Trp | 3 | — | — |
| Tyr | 1 | 1,1 | 1,7 |
| Val | 6 | 5,8 | 6,2 |

Mass spectrometry. Laser desorption mass spectra of gloverin (FIG. 3) indicated a molecular mass of 13786 Da, which is in good agreement with the value of 13785 Da as calculated from the amino acid sequence. There is no indication that gloverin is glycosylated, although there is a potential glycosylation site at asparagine 87.

Conformational studies. The CD-spectrum of gloverin in 10 mM phosphate, pH 6.4, can be interpreted as a reflection of a mainly random-coil structure (FIG. 4). To estimate the possible structure present in a more hydrophobic, membrane-like environment, CD-spectra were recorded in different concentrations of hexafluoro-iso-propanol. In a hydrophobic environment the spectrum changes to reflect a conformation having large amounts (approx. 50%) of alpha-helix structure (FIG. 4). The degree of assumed alpha-helix reaches a maximum at a concentration of 20% of hexafluoro-iso-propanol. The result from the NMR-analysis confirms the conformational change that was indicated by the CD experiments (data not shown).

From the ultracentrifugation sedimentation experiments of gloverin in 10 mM phosphate, pH 6.4, the following parameters were calculated: sedimentation coefficient (S°20 (w))=1.4 S, diffusion coefficient (D)=8.95×10−7 cm2s−1 and a friction ratio (f/f0)=1.5. These values are in accordance with the expected values to be obtained for a protein of estimated molecular weight of 13.8 kDa and present in an extended conformation.

The equilibrium experiments gave a molecular weight of 13.8 kDa showing that the protein exists as a monomer in water solution.

Antibacterial activity.

The growth of *E. coli* K-12 is inhibited. Addition of gloverin to growing cultures of sensitive *E. coli* caused a decrease in the growth rate. This effect was noticeable after 1 h. After 2–3 h, growth was completely inhibited (FIG. 5) and prolonged exposure to gloverin resulted in a decrease in cell density. The remaining cells were still viable since the cultures recovered and continued to grow when incubated over night (data not shown).

Included in FIG. 5 is also a viable count experiment showing the correlation between cell density and the number of viable cells. No inhibitory effect of gloverin on the gram-positive cell *Bacillus megaterum* could be observed, using concentrations of up to 100 mM of gloverin (not shown). The growth-inhibiting effect of gloverin is not significantly affected by heating the protein to 100° C. for 10 min (data not shown).

The permeability of the outer membrane increases. Addition of the non-ionic detergent Triton X-100 to a culture of *E. coli* D21f2 grown for 2.2 h in the presence of gloverin resulted in a drastic drop in absorbance, in contrast to the much smaller effect of Triton X-100 on untreated control cultures (FIG. 6). The sensitivity to lysozyme was also icreased by gloverin-treatment (FIG. 6). These results suggest that gloverin affects the integrity of the outer membrane, allowing entry of substances that are normally excluded by this permeability barrier, such as conventional antibiotics. Combined therapy with gloverin and conventional antibiotic(s) will lower the dose normally required for the antibiotic(s).

Mg2+ inhibits the activity of gloverin. The effect of gloverin on the growth of D21f2 was inhibited in the presence of 40 mM Mg2+ (FIG. 7B). This result is in accordance with the role of magnesium in stabilising the outer membrane. Binding to free LPS inhibits activity. Pre-incubation of gloverin with soluble LPS (Rd)(Sigma) for 30 min at 37° C. prior to addition of the mixture to a growing culture of D21f2 cells blocks the antibacterial effect of gloverin (FIG. 7A). The inhibitory effect of LPS is concentration-dependent.

The synthesis of outer membrane proteins is affected. SDS-PAGE analysis of the protein content of gloverin-treated and radioactively labelled D21f2 cells showed that there was no general effect on protein synthesis. However, gloverin caused a specific inhibition of the synthesis of the outer membrane proteins Omp F, Omp C and Omp A. Some additional, unidentified proteins were also affected (FIG. 8).

DISCUSSION

A novel, antibacterial protein isolated from the immune hemolymph of *Hyalophora gloveri* pupae, is described in functional and structural terms.

The studied gloverin has a molecular mass of 13785 Da and consists of 130 amino acids without any cysteines but with a high content (18.5%) of glycine. Ultracentrifugation and circular dichroism show that gloverin exists as a monomeric random coil in water solution, while, according to circular dichroism, an alpha helix structure can be induced by the addition of hexafluoro-iso-propanol. The direct measurement of molecular weight by mass spectrometry compared to the mass deduced from the amino acid sequence indicates that the gloverin is not subject to post-translational modifications, e.g. glycosylation.

A protein corresponding to gloverin was isolated from the closely related lepidopteran *Hyalophora cecropia* and the sequence for the 38 N-terminal amino acids was found to be identical. Also the amino acid analysis for the two proteins gave similar results. Comparison of the gloverin sequence with those of other proteins found in the data base disclosed no structural similarity to known proteins. Thus, we conclude that gloverin represents a novel class of antibacterial proteins.

The antibacterial effect of gloverin seems to be directed towards certain gram-negative bacteria. The sensitivity of *E. Coli* K-12 increases with decreasing length of the polysaccharide chain of the lipopolysaccharide (LPS). Strain D21f2 used in the experiments is an LPS mutant with an Re-type of LPS, and the most sensitive strain. The parent strain D21(LPS Ra) is about 10 times less sensitive. The fact that gloverin renders these bacteria sensitive to the detergent Triton X-100 and to lysozyme, —compounds that are normally inactive against these cells due to their inability to penetrate the outer membrane—indicates that gloverin has an effect directed against the cell envelope. This effect could be almost completely inhibited by Mg2+ that is known to have an important role in stabilisation of the outer membrane of gram-negative bacteria. The observed increase in permeability is accompanied by a decrease in outer membrane proteins, an effect which further indicates that the outer membrane is the target for gloverin.

The observation that the sensitivity of the cell to gloverin increases with decreasing length of the polysaccharide chain of LPS, in combination with the fact that the effect of gloverin on growth is inhibited by pre-incubation with LPS in solution, indicates that binding to LPS is important for the action of gloverin. The polysaccharide chains of LPS may hinder gloverin simply by steric interactions. The shorter the chain, the easier it is for gloverin to get access to the inner parts of the LPS-layer. Possible binding sites for the basic gloverin might be provided by the lipid A part of LPS and/or the phosphate groups present both on lipid A and on the 2-keto-3-deoxyoctonic acid (KDO). The activity of gloverin resembles in many respects (permeability, Omp synthesis, inhibition by free LPS) that of attacin (6,7)

A comparison of gloverin and mammalian BPI, shows that the effect of BPI is also inversely dependent of the length of the LPS polysaccharide chains [14]. Addition of magnesium ions also inhibits the effect of BPI. However, in contrast to gloverin and attacin, BPI does not seem to have the same profound effect on the synthesis of outer membrane proteins [15]. Gloverin retains its antibacterial properties after boiling which shows that the activity is not due to any catalytic effect. This is also true for the attacins, cecropins and BPI.

The novel antibacterial proteins of the invention enable new antimicrobial therapy with new antimicrobial agents, i.e. gloverins. Gloverin can be combined with other conventional antimicrobial agents, such as penicillins, to enhance the antimicrobial effect. Furthermore, they provide useful tools for studies of the regulation of assembly and synthesis of the bacterial outer membrane.

REFERENCES

1. Boman H. G., Faye I., Gudmundsson G. H., Lee J-Y & Lindholm D. A. (1991) Cell-free immunity in Cecropia. A model system for antibacterial proteins, Eur. J. Biochem. 201, 23–31.
2. Powning R. F. & Davidson W. J. (1976) Studies on insect bacteriolytic enzymes-II. Some physical and enzymatic properties of lysozyme from hemolymph of *Galleria mellonella*, Comp. Biochem. Physiol. 55, 221–228.
3. Hultmark D., Steiner H., Rasmuson T., & Boman H. G. (1980) Insect immunity: purification and properties of three inducible bactericidal proteins from hemolymph of immunized pupae of *Hyalophora cecropia*, Eur. J. Biochem. 106, 7–16.
4. Steiner H., Hultmark D., Engström Å., Bennich H. & Boman H. G. (1981) Sequence and specificity of two antibacterial proteins involved in insect immunity, Nature 292, 246–248.
5. Hultmark D., Engström A., Andersson K., Steiner H., Bennich H. & Boman H. G. (1983) Insect immunity. Attacins, a family of antibacterial proteins from *Hyalophora cecropia*, EMBO J. 4, 571–576.
6. Engström P., Carlsson A., Engström E., Tao Z-J. & Bennich H. (1984) The antibacterial effect of attacins from the silk moth *Hyalophora cecropia* is directed against the outer membrane of *Escherichia coli*, EMBO J. 3, 3347–3351.
7. Carlsson A., Engström P., Palva E. T. & Bennich H. (1991) Attacin, an antibacterial protein from *Hyalophora cecropia*, inhibits synthesis of outer membrane proteins in *Escherichia coli* by interfering with omp gene transcription, Infect. Immun. 59, 3040–3045.
8. Lee, J.-Y., Boman, A., Sun, C., Andersson, M., Jörnvall, H., Mutt, V. & Boman, H. G. (1989) Antibacterial peptides from pig intestine: isolation of a mammalian cecropin, Proc. Natl. Acad. Sci. USA 86, 9159–9162.
9. Ando K. & Natori S. (1988) Inhibitory effect of sarcotoxin IIA, an antibacterial protein of Sarcophaga peregrina, on growth of *Escherichia coli*, J. Biochem. 103, 735–739.
10. Hoffman J. A. & Hetru C. (1992) Insect defensins: inducible antibacterial peptides, Immunol. Today. 13, 411–415.
11. Keppi E. Pugsley A. P. Lambert J. Wicker C. Dimarcq J-L., Hoffman J. A. & Hoffman D. (1989) Mode of action of diptericin A, a bactericidal peptide induced in the hemolymph of *Phormia terranovae* larvae, Arch. Insect. Biochem. Physiol. 10, 229–239.
12. Sun S-C., Lindström I., Boman H. G., Faye I. & Schmidt O. (1990) Hemolin: An insect immune protein belonging to the immunoglobulin superfamily, Science. 250, 1729–1732.
13. Ladendorff N. E. & Kanost M. R. (1991) Bacteria-induced protein P4 (hemolin) from *Manduca sexta*: A member of the immunoglobulin superfamily which can inhibit hemocyte aggregation, Arch. Insect Biochem. Physiol. 18, 285–300.
14. Elsbach P. & Weiss J. (1993) Immunobiol. 187, 417–429.
15. Elsbach P. & Weiss J. (1986) Phagocytic cells: Oxygen-independent antimicrobial systems, in Inflammation: Basic principles and clinical correlates (Gallin J. I., Goldstein I. M. & Snyderman R., eds) pp. 445–470, Raven Press Ltd, New York.
16. Lehrer R. I., Lichtenstein A. K & Ganz T. (1993) Defensins: Antimicrobial and cytotoxic peptides of mammalian cells, Annu. Rev. Immunol. 11, 105–128.
17. Laemmli U. K. (1970) Cleavage of structural proteins during the assembly of the head of bacteriophage T4, Nature 277, 680–685.
18. Edman P. & Begg G. (1967) A protein sequenator, Eur. J. Biochem. 1, 80–91.
19. Pearson W. P. & Lipman D. J. (1988) Improved tools for biological sequence comparison, Proc. Natl. Acad. Sci. USA 85, 2444–2448.
20. Devereaux J., Haeberli P. & Smithies O. (1984) A comprehensive set of sequence analysis programs for the VAX, Nucleic Acid Res. 12, 387–395.
21. Boman H. G. & Monner D. A. (1975) Characterization of lipopolysaccharides from *Escherichia coli* K-12 mutants, J. Bact. 121, 455–464.

22. Boman H. G. Eriksson-Grennberg K. G., Normark S. & Matsson E. (1968) Resistance of *Escherichia coli* to penicillins. IV. Genetic study of mutants resistant to D, I-ampicillin concentrations of 100 ug/ml, Genet. Res (Cambridge) 12, 169–185.

23. Rasmuson T. & Boman H. G. (1977) in Developmental Immunology (Solomon J. B & Horton J. D., eds) pp. 83–90, Elsevier/North-Holland Biomedical Press, Amsterdam.

8. A pharmaceutical composition according to claim 7, characterized by comprising conventional antibacterial agent(s) in addition to said antibacterial protein or fragments.

9. A pharmaceutical composition according to claim 8, characterized in that the conventional antibacterial agents are antibiotics and/or cell degrading agents, such as enzymes and detergents.

SEQUENCE LISTING

```
<160> NUMBER OF SEQ ID NOS: 1

<210> SEQ ID NO 1
<211> LENGTH: 130
<212> TYPE: PRT
<213> ORGANISM: Lepidoptera

<400> SEQUENCE: 1

Asp Val Thr Trp Asp Lys Asn Ile Gly Asn Gly Lys Val Phe Gly Thr
  1               5                  10                  15

Leu Gly Gln Asn Asp Asp Gly Leu Phe Gly Lys Ala Gly Phe Lys Gln
             20                  25                  30

Gln Phe Phe Asn Asp Asp Arg Gly Lys Phe Glu Gly Gln Ala Tyr Gly
         35                  40                  45

Thr Arg Val Leu Gly Pro Ala Gly Gly Thr Thr Asn Phe Gly Gly Arg
     50                  55                  60

Leu Asp Trp Ser Asp Lys Asn Ala Asn Ala Ala Leu Asp Ile Ser Lys
 65                  70                  75                  80

Gln Ile Gly Gly Arg Pro Asn Leu Ser Ala Ser Gly Ala Gly Val Trp
                 85                  90                  95

Asp Phe Asp Lys Asn Thr Arg Leu Ser Ala Gly Gly Ser Leu Ser Thr
            100                 105                 110

Met Gly Arg Gly Lys Pro Asp Val Gly Val His Ala Gln Phe Gln His
        115                 120                 125

Asp Phe
    130
```

We claim:

1. An antibacterial protein against gram negative bacteria, characterized by having an approximative molecular weight of 14 kD and an approximative isoelectric point of 9.

2. An antibacterial protein according to claim 1, derived from Lepidoptera.

3. An antibacterial protein according to claim 2, derived from Hyalophora moths, wherein the molecular weight is approximately 13.8 kD and the pl is 8.5.

4. An antibacterial protein according to claim 3, characterized by having SEQ ID NO:1 or an amino acid sequence substantially homologous therewith.

5. An antibacterial protein according to claim 4, characterized by being encoded by a DNA sequence derived from SEQ ID NO:1 or from an amino acid sequence substantially homologous therewith.

6. An antibacterial protein according to claim 1, produced by genetic engineering or chemical synthesis.

7. A pharmaceutical composition, characterized by comprising antibacterial protein according to claim 1 or any antibacterially active fragment thereof.

10. An antibacterial protein according to claim 1 or pharmaceutically active fragments thereof for use as a medicament.

11. A method for using an effective amount of an antibacterial protein according to claim 1 to treat infections caused by gram-negative bacteria.

12. A method for using an effective amount of an antibacterial protein according to claim 1 in combination with other conventional antibacterial agent(s) to treat bacterial infection.

13. A method of treating bacterial infection in a subject, characterized in that an antibacterial protein according to claim 1 is administered to said subject in an effective amount.

14. A method according to claim 13, characterized in that said antibacterial protein is co-administrated with conventional antibacterial agent(s).

15. A pharmaceutical composition, characterized by comprising antibacterial protein according to claim 2 or any antibacterially active fragment thereof.

16. A pharmaceutical composition, characterized by comprising antibacterial protein according to claim 3 or any antibacterially active fragment thereof.

17. A pharmaceutical composition, characterized by comprising antibacterial protein according to claim 4 or any antibacterially active fragment thereof.

18. A pharmaceutical composition, characterized by comprising antibacterial protein according to claim 5 or any antibacterially active fragment thereof.

19. A pharmaceutical composition, characterized by comprising antibacterial protein according to claim 6 or any antibacterially active fragment thereof.

* * * * *

UNITED STATES PATENT AND TRADEMARK OFFICE

CERTIFICATE OF CORRECTION

PATENT NO. : 6,063,765
DATED : May 16, 2000
INVENTOR(S) : Hans BENNICH et al.

It is certified that error appears in the above-indentified patent and that said Letters Patent is hereby corrected as shown below:

On the title page, insert Item [30] as follows:

--[30] Foreign Application Priority Data

Jan. 28, 1997 [SE] Sweden............ 9700244.8--.

Signed and Sealed this

Sixth Day of March, 2001

Attest:

NICHOLAS P. GODICI

*Attesting Officer*

*Acting Director of the United States Patent and Trademark Office*